(12) United States Patent
Henniges et al.

(10) Patent No.: US 6,592,578 B2
(45) Date of Patent: Jul. 15, 2003

(54) DEVICE FOR LOCALLY HEATING A BIOABSORBABLE PLATE

(75) Inventors: Bruce D. Henniges, Kalamazoo, MI (US); Paul T. Longo, Kalamazoo, MI (US); Douglas L. Tyler, Sr., Paw Paw, MI (US)

(73) Assignee: Howmedica Leibinger, Inc., Kalamazoo, MI (US)

( * ) Notice: Subject to any disclaimer, the term of this patent is extended or adjusted under 35 U.S.C. 154(b) by 0 days.

(21) Appl. No.: 09/791,357

(22) Filed: Feb. 23, 2001

(65) Prior Publication Data

US 2002/0004660 A1 Jan. 10, 2002

Related U.S. Application Data

(60) Provisional application No. 60/184,613, filed on Feb. 24, 2000.

(51) Int. Cl.$^7$ .................................................. A61B 18/04
(52) U.S. Cl. .................. 606/27; 222/146.1; 222/189.06
(58) Field of Search .............................. 606/27–31, 101; 219/227, 229; 222/146.1, 146.2, 146.5, 189.06, 189.09; 604/215; 99/345

(56) References Cited

U.S. PATENT DOCUMENTS

| | | | |
|---|---|---|---|
| 3,128,920 A | * 4/1964 | Volckening et al. | 206/484 |
| 3,459,335 A | * 8/1969 | Cohen et al. | 219/227 |
| 3,534,731 A | 10/1970 | Muller | |
| 3,695,259 A | 10/1972 | Yost | |
| 3,715,060 A | * 2/1973 | Benson | 222/207 |
| 4,249,899 A | * 2/1981 | Davis | 222/146.5 |
| 4,512,038 A | 4/1985 | Alexander et al. | |
| 4,581,021 A | * 4/1986 | Landau et al. | 222/103 |
| 4,905,680 A | 3/1990 | Tunc | |
| 5,290,281 A | 3/1994 | Tschakaloff | |
| 5,607,427 A | 3/1997 | Tschakaloff | |
| 5,779,706 A | 7/1998 | Tschakaloff | |
| 5,787,799 A | * 8/1998 | Mohrhauser et al. | 222/215 |
| 5,944,721 A | 8/1999 | Huebner | |
| 5,968,046 A | 10/1999 | Castleman | |
| 6,159,007 A | * 12/2000 | Sorensen | 210/321.64 |

* cited by examiner

*Primary Examiner*—Eduardo C. Robert
*Assistant Examiner*—Michael B. Priddy
(74) *Attorney, Agent, or Firm*—Howard & Howard

(57) ABSTRACT

The present invention is a system for installing bioabsorbable plates for general bone repair, as for example, facial or cranial osteosynthesis. The present invention includes an improved plate and fastener system which reduces if not eliminates stresses within the plate. It also includes an improved fastener container and driver for handling and installing fasteners. The system employs a unique water bath for heating the bioabsorbable plate so they can be deformed to the contours of the bone being repaired. Additionally, there is a hand tool for localized heating and deformation of the plate when positioned against the bone to further ensure conformity with the bone structure. These and other features are contained within a kit which is easily sterilized.

24 Claims, 10 Drawing Sheets

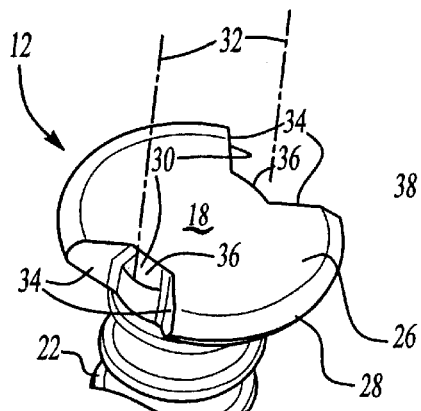
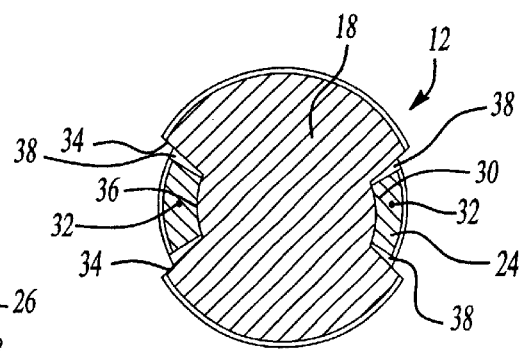
*Fig-6A*  *Fig-6B*
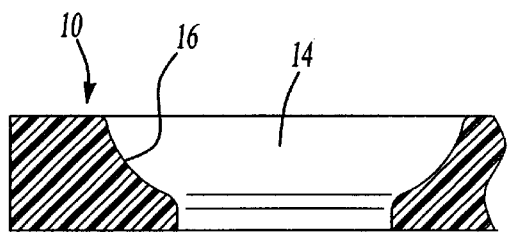
*Fig-7*
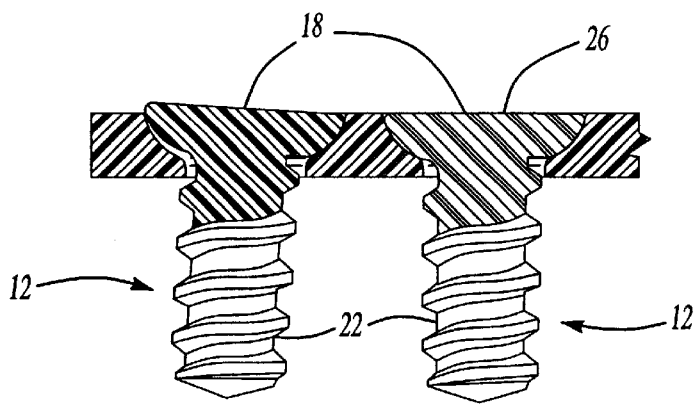
*Fig-8*
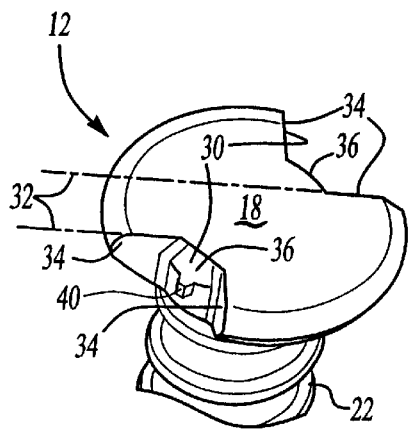
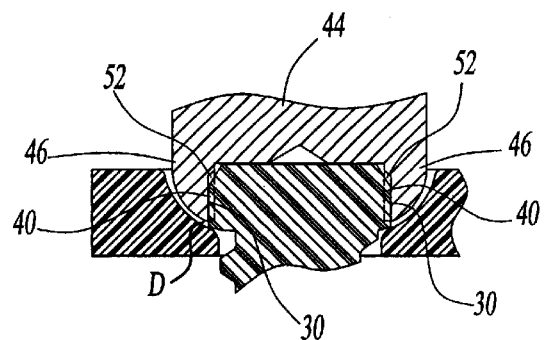
*Fig-9*  *Fig-10*

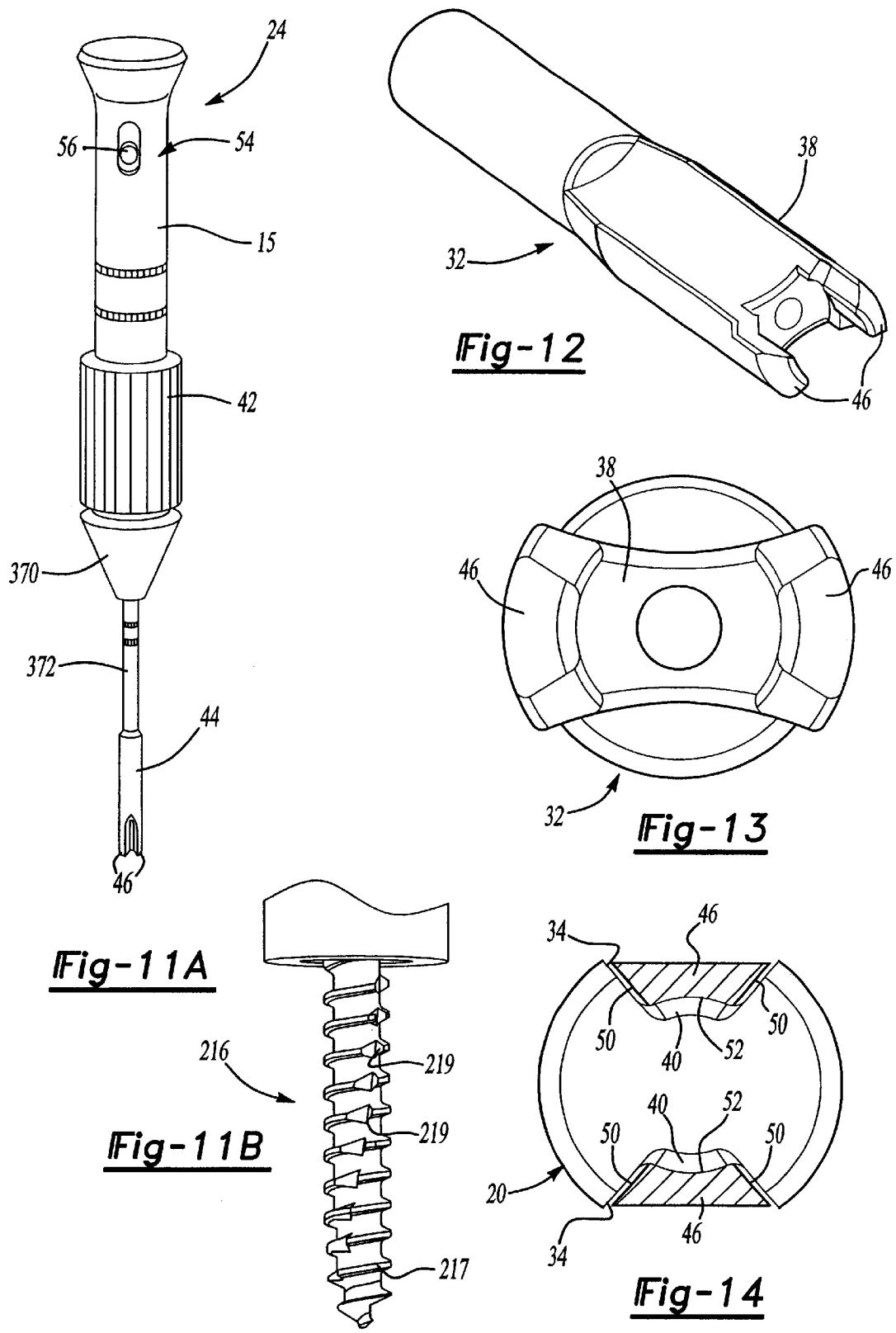

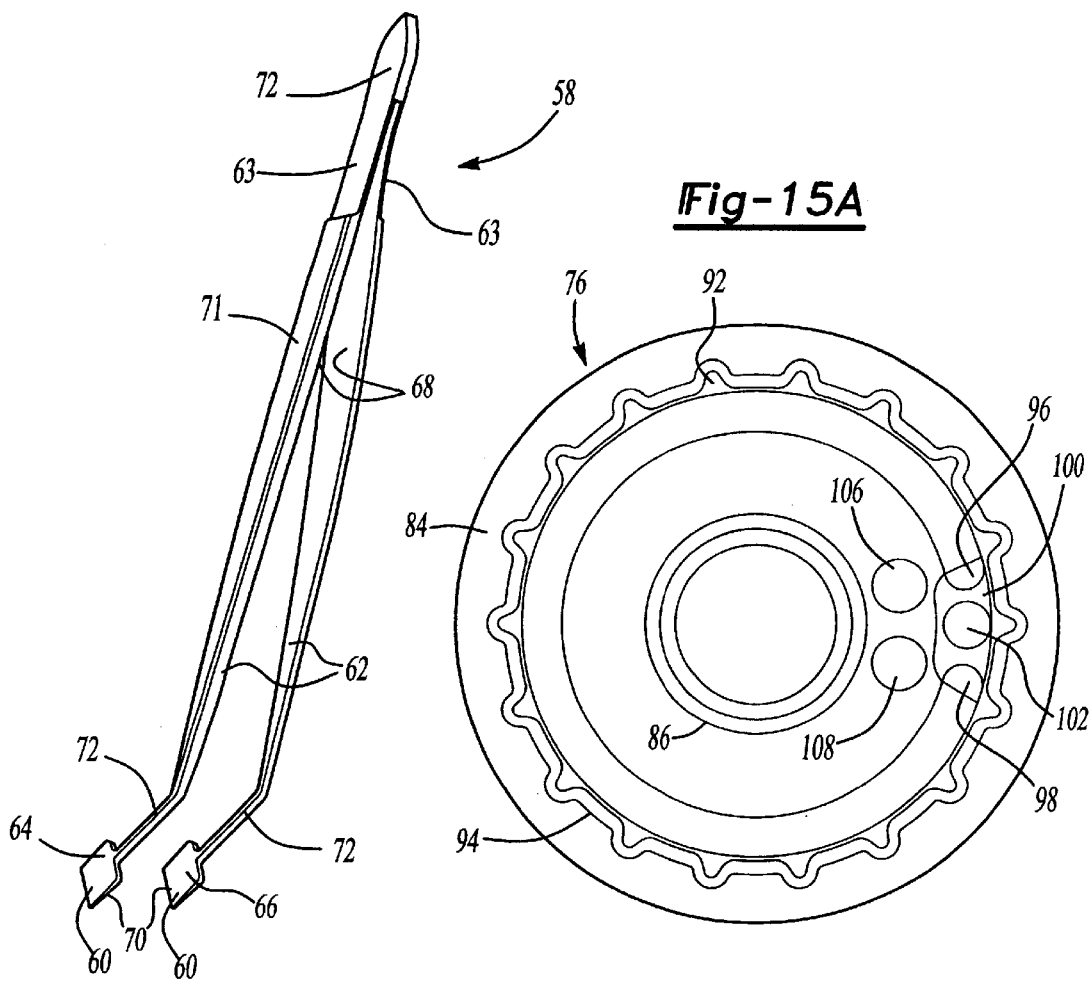
*Fig-15*
*Fig-15A*
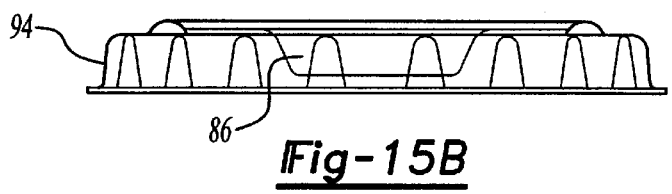
*Fig-15B*
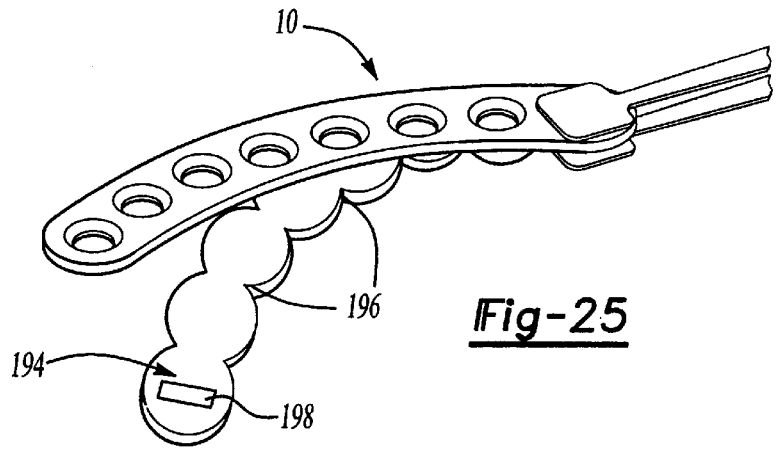
*Fig-25*

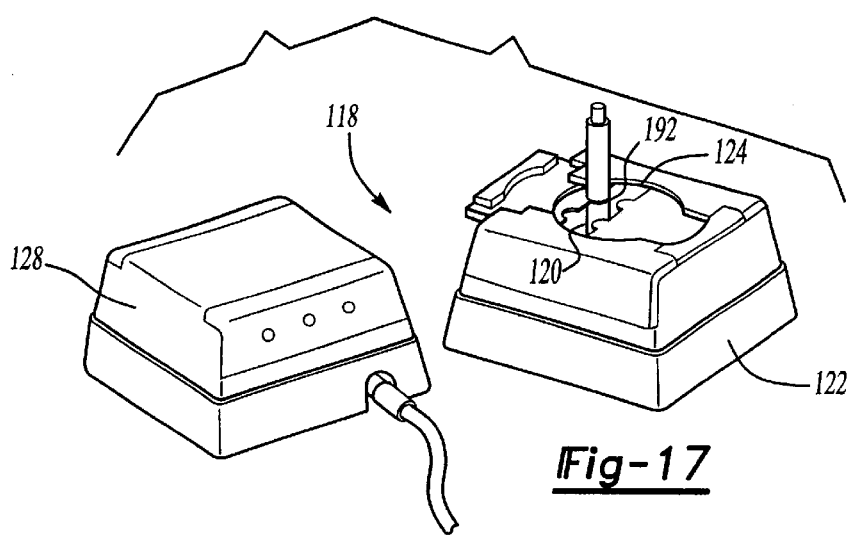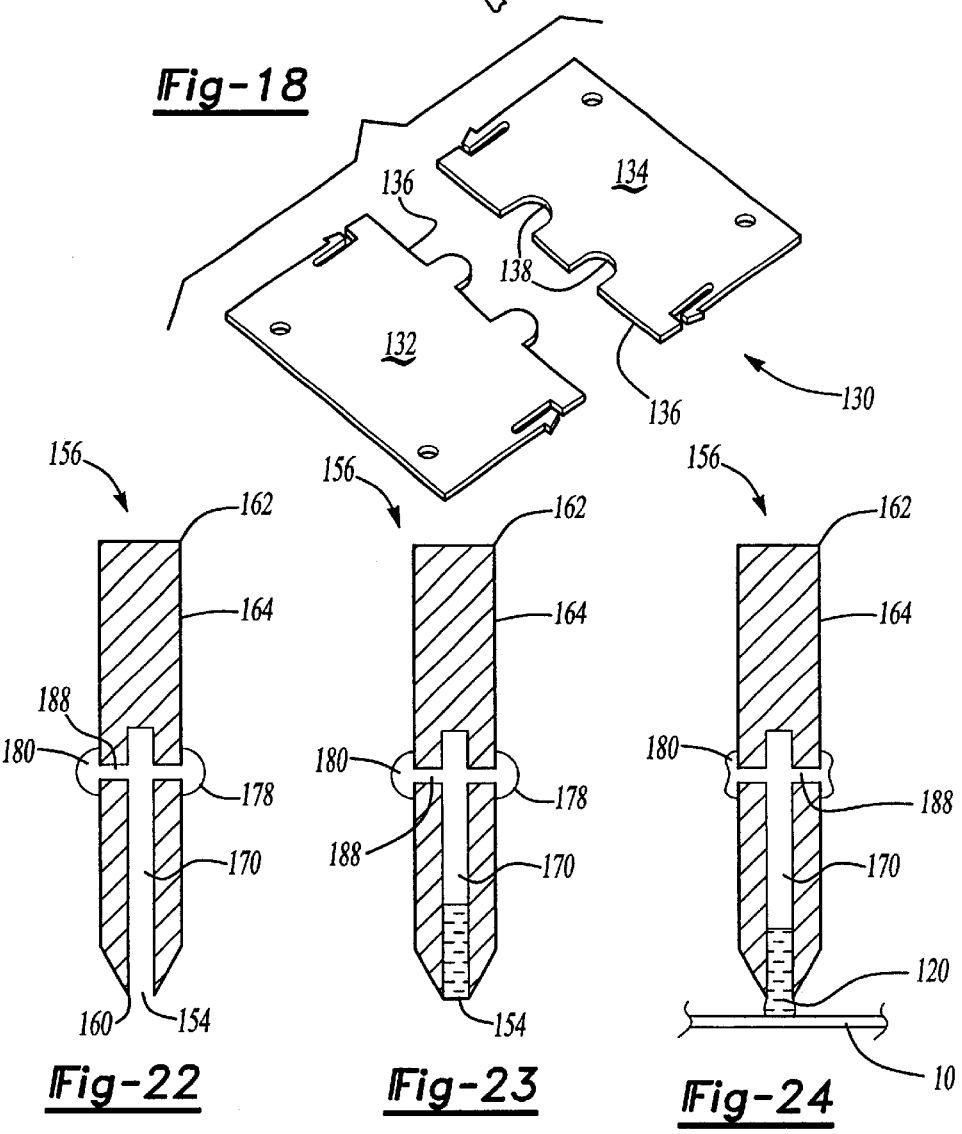

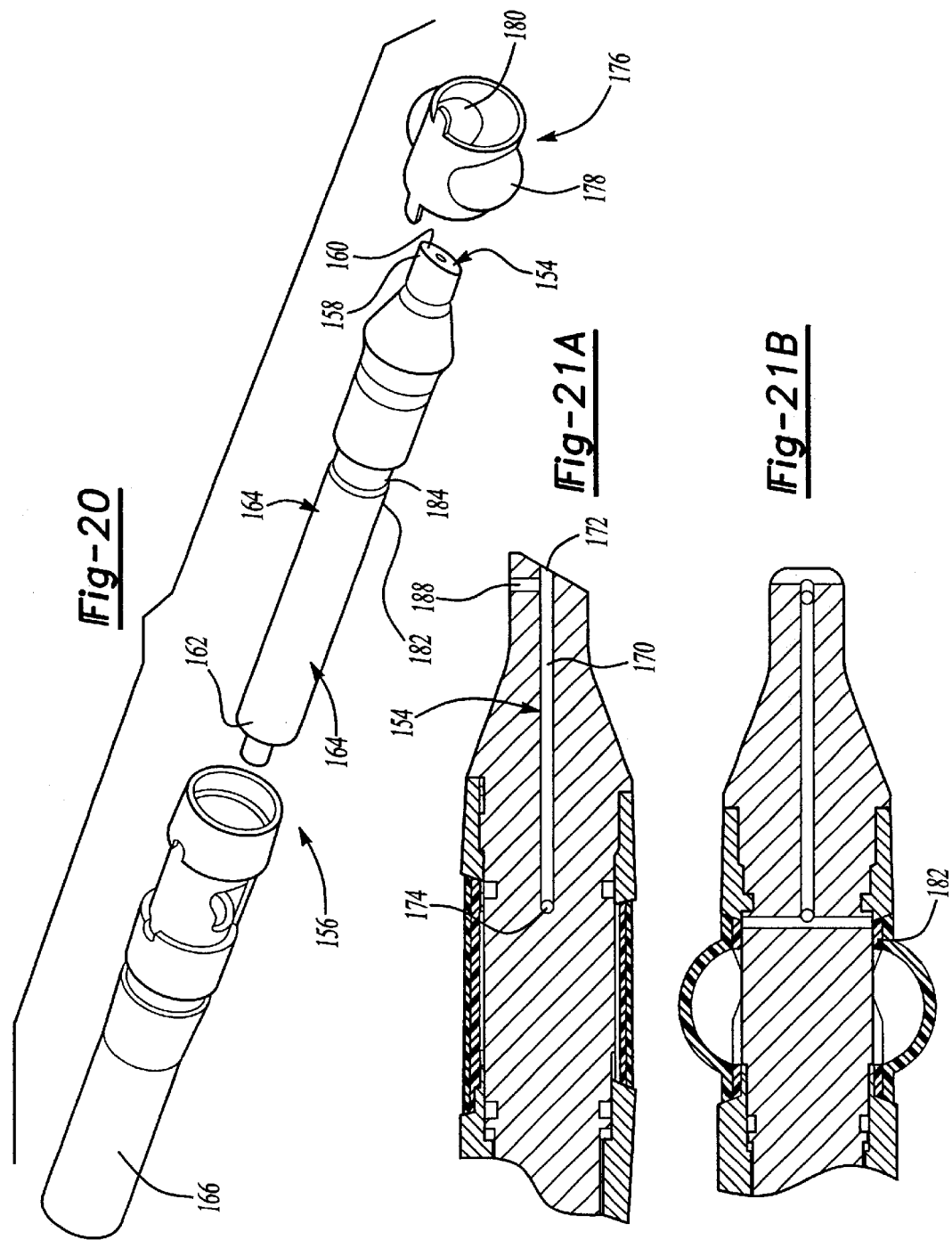

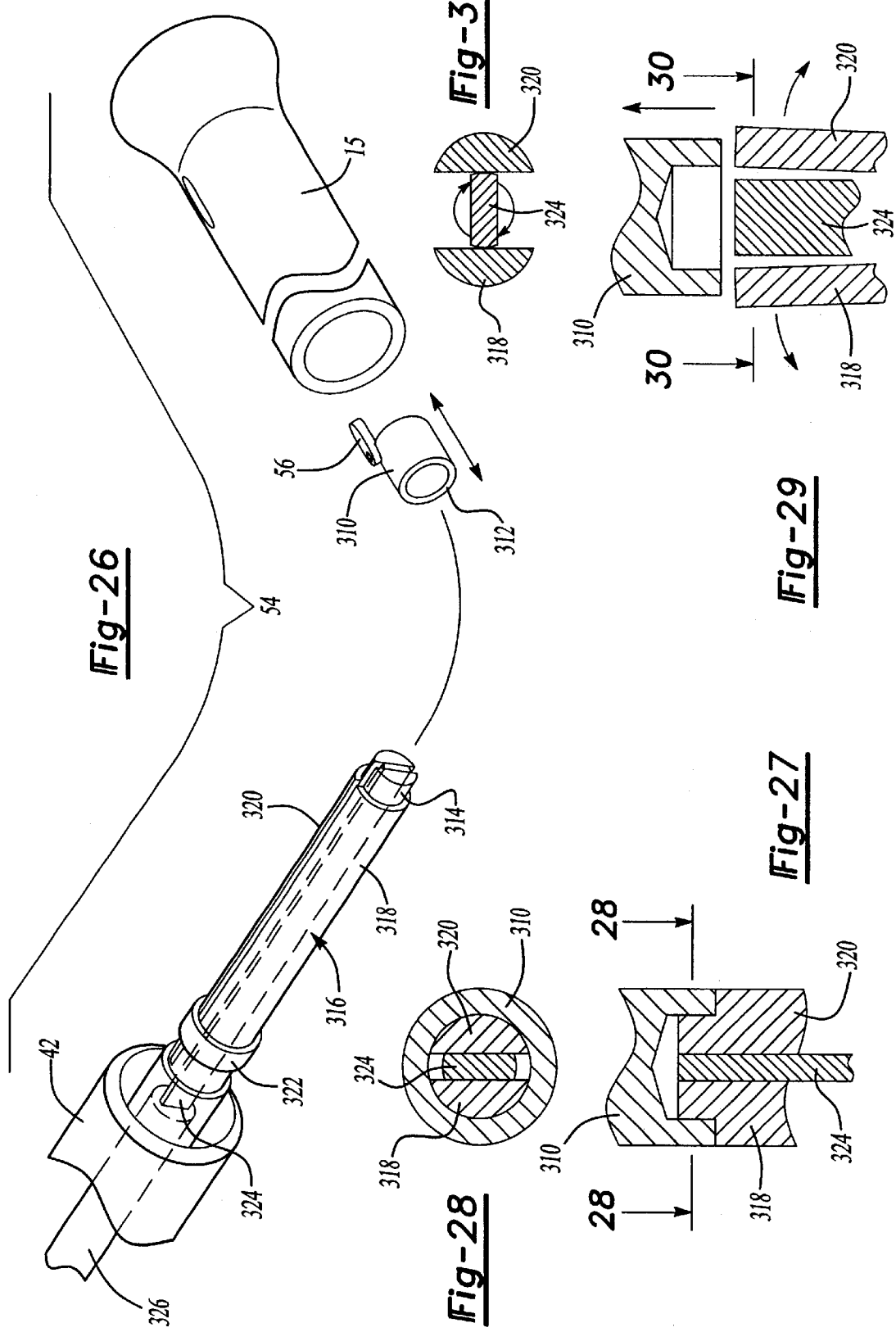

DEVICE FOR LOCALLY HEATING A BIOABSORBABLE PLATE

This application claims the benefit of U.S. Provisional Patent Application Ser. No. 60/184,613, filed Feb. 24, 2000.

BACKGROUND OF THE INVENTION

The use of bioabsorbable plates to repair bone fractures, particularly factures to the craniofacial skeleton is known. In this procedure, a bioabsorbable plate is used to hold bone together to allow a fracture to heal. The plate is generally formed to the bone and held in place by screws. Bioabsorbable plates are normally rigid, become soft or malleable when heated, and return to being rigid when cooled. Typically, a bioabsorbable plate is heated in some manner to make it easily deformable so that the plate can be formed to the bone. Either before or after the plate is formed to the bone, a drill is used to drill holes into the bone. The drilled holes are then tapped and screws are positioned within openings in the plates and threaded into the tapped holes to hold the plates in position.

One problem with known systems for applying bioabsorbable plates is that the plate doesn't remain soft for long. Once it is heated, the surgeon must fairly quickly form the plate to the bone structure. If the surgeon doesn't get the plate properly formed before it cools, then the plate must be heated again and the forming process started over. As should be appreciated, this can become a very tedious process and result in loss of time during the surgical procedure. Additionally, the surgeon has no means for spot heating the plate to deform a specific spot or portion on the plate to better conform the plate to the bone.

Another problem with known bioabsorbable plates is that the attached screws can create stresses within the plates. In the event that a screw is not threaded into a tapped hole in proper alignment, the screw may only contact the plate with point contact. In this event, the plate may crack or loosen due to the uneven force distribution. Obviously, this would be a problem, particularly if the problem is not discovered until after stitches have been applied.

A problem with known bioabsorbable screws is there tendency to break due to their design. Although bioabsorbable screws are very strong, they can break off while being threaded into the tapped hole or when being tightened. Once broken, the screw generally must be drilled out of the bone, a new larger hole drilled and retapped and a larger screw threaded into the tapped hole. Again, this is a tedious process and one which creates difficulties during an operation.

Another problem with known bioabsorbable systems are the techniques for heating the bioabsorbable plates. The most common method for heating the bioabsorbable plates is to place them in a hot water bath which sufficiently heats the plate for it to be deformable. Because the hot water bath has to be within the sterile field of the surgery room, it must be capable of being sterilized. Typically, the water bath amounts to a stand draped with a cloth and a sterilized bowl to contain hot water. The surgeon can then dip the bioabsorbable plates into the hot water and conform them to the bone surface.

Another problem with known surgical systems to fasten bioabsorbable plates to bone structure is the complicated system used to match a request by a surgeon for a particular plate with the actual template. Typically, extensively long alpha numeric codes are used which result in the possibility of confusion between the request by the doctor and the filling of that request by an attendant.

SUMMARY OF THE INVENTION

The present invention overcomes the above problems by providing a bioabsorbable plate that has a first thermochemical solid state which is rigid and a second thermochemical solid state which is deformable so that it can be easily formed to the bone. The plate includes a plurality of at least two openings for receiving a fastener with a relief area surrounding each of the openings to allow the fastener to seat within the bioabsorbable plate so that no part of the fastener extends above the surface of the plate when the fastener is applied. The relief area presents a generally concave surface surrounding each of the openings. The relief area provides a stable contact surface for the fastener. This reduces tensile stresses in the plate and allows proper seating of the fastener within the relief area when the fastener is inserted either properly or at an angle that is not perpendicular to the plate.

The fastener of the present invention includes a head and shank portion. The head contacts the bioabsorbable plate to hold the bioabsorbable plate against the bone surface to be repaired. The shank portion extends from the head portion and includes threads for providing threaded engagement with the bone surface being repaired. The head portion includes at least one recess for insertion of a driver to allow the fastener to be threaded into the bone surface being repaired. This head portion includes a bottom surface presenting a generally convex contour for contacting a concave relief within the bioabsorbable plate. This convex contour mating with the concave relief ensures that the screw head will have at least line contact with the plate and preferably surface contact. This enhances the fastening of the plate to bone and reduces if not eliminates the problem of tensile stresses in the plate due to misaligned screws.

In the disclosed embodiment of the fastener of the present invention, the head portion includes a pair of notches. The notches include a pair of side walls and a rear wall. The notches are oriented 180 degrees apart about the circumference of the head portion of the fastener. The notches are sized to receive features of the driver, and the side walls providing a contact surface for the driver to thread the fastener into place. The positioning of the side walls distributes forces applied to the screw through the head as compressive forces because the side walls are not through the centerline of the fastener. The side walls for each of the notches fall on lines that cross at a point outside the centerline of the head portion, thereby concentrating the forces exerted onto the head portion into compressive stresses within the head portion to reduce failure.

The present invention also includes a driver for threading the fasteners into bone. The driver includes an operative end for engagement with a fastener, a handle portion opposite the operative end for allowing manual manipulation of the driver to insert the fastener, and a clutch mechanism interconnecting the handle portion and the operative end for limiting the amount of torque that can be transferred. The handle portion includes a switch for selectively activating the clutch mechanism. The operative end includes a pair of fingers, each of the fingers including side walls and an internal wall. The side walls are spaced to fit within notches in the head portion of the fastener. The fingers have a thickness that is less than the depth of the notches on the fastener to allow the fingers to fit completely within the circumference of the head portion of the fastener to prevent interference with the bioabsorbable plate when the fastener is applied using the driver.

Another advantage of the present invention is the use of a unique portable bowl for containing a volume of heated fluid. The bowl includes a base, a reservoir for holding a volume of heated fluid, and a heating element disposed within the base for heating the fluid within the reservoir. A controller for controlling the heating element and maintaining the temperature of the heated fluid within the reservoir is located at a remote location from the bowl. In this way, the bowl can be easily sterilized without having to sterilize the more difficult to sterilize controller. The portable bowl includes a retractable cover assembly for keeping the heated fluid within the bowl and to assist in keeping the fluid at a predetermined temperature. The cover assembly includes features for holding tools to allow the tools to extend into the heated fluid within the portable bowl.

In addition to the portable bowl, the present invention includes an apparatus for applying a heated fluid to a localized portion of a bioabsorbable plate. The device includes a front end with a tip, a rear end, and a shaft portion interconnecting the front end and the rear end. A cavity is disposed on the tip to hold a droplet of the heated fluid to the tip when the tip is dipped within the heated fluid or to draw heated water into the cavity to be dispensed when desired. The tool allows a surgeon to heat the plate at a localized point without having to reheat the entire plate.

The present invention also includes a dispenser for holding and delivering fasteners to a point of use. The dispenser includes a tray for holding a plurality of fasteners, a lid mounted rotatably onto the tray for keeping the fasteners contained until used, and an opening to allow the fasteners to be removed from the tray. The tray has a plurality of apertures spaced radially about the tray. Each aperture is adapted to removably hold one fastener in vertical orientation. The lid includes a first opening and a second opening spaced to fall directly above the apertures when the lid is rotated and adapted to allow an operable end of a driver to be inserted into the tray to engage and remove the fastener from one of the apertures. There are a plurality of detents spaced radially around the outer circumference of the tray, the lid includes at least one indent for receiving one of the plurality of detents, so that the lid can be rotated between a plurality of radial positions. The detents are spaced such that as the lid rotates, the pair of openings within the lid move from a first position wherein the first opening is directly over one of the apertures and the second opening is positioned between two of the apertures, a second position where both the first and second openings are located directly above one of the apertures, and a third position wherein both the first and second openings are located between two of the apertures.

The invention further includes a device for handling bioabsorbable plates. The device includes a pair of flexible elongated arms in adjacent lengthwise relationship with one another, each arm having a first end and a second end. The first ends of the arms are secured to one another, with the second ends of the arms being disposed at a distance from one another. A generally flat protruding portion is attached to the second end of each of the arms, the protruding portions of each arm being oriented parallel to one another. This device allows the plates to be held without damage to the plates.

To assist in forming the plates to the contour of the bone surface, a template for capturing the contour of a bone structure to be repaired is provided. The template allows the plate to be pre-contoured, wherein the template presents a two-dimensional shape that roughly corresponds to the two-dimensional shape of the plate that is to be contoured. In the preferred embodiment, the template has indents that correspond to the locations of fastener openings within the plate. In the most preferred embodiment, the template is made from a malleable material which is autoclavable to allow the template to be sterilized and re-used. In another embodiment, the template is a block having a top and bottom surface, and including a plurality of through holes extending between the top and bottom surfaces. A plurality of pins are disposed within the holes. A locking device locks the pins within the through holes to prevent the pins from sliding therein. The position of the pins are changed when pressed against the bone structure to give a three dimensional view of the bone contour. The pins can then be locked in place and the plate deformed to the contour of the pins.

All of these items are preferrably contained within a kit that can be easily sterilized and taken to the sterile surgical field. Additionally, the present invention includes the method of using the above items to fasten fractured bone pieces together. Still further, the present invention includes a unique coding system to simplify the surgical procedure.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 6A is a perspective view of the fastener of the present invention;

FIG. 6B is a cutaway view of the fastener of the present invention;

FIG. 7 is a side cut away view of the opening and relief area within the bioabsorbable plate;

FIG. 8 is a cut away view of the opening within the bioasborbable plate and fastener;

FIG. 9 is a perspective view of the fastener of the present invention;

FIG. 10 is a cutaway view of the plate, fastener and driver of the present invention;

FIG. 11A is a perspective view of the driver of the present invention;

FIG. 11B is a perspective view of the drill bit tool of the present invention;

FIG. 12 is a perspective view of the end of the driver of the present invention;

FIG. 13 is an end view of the driver of the present invention;

FIG. 14 is a view of the fastener attached to the driver;

FIG. 15 is a perspective view of a pair of forceps of the present invention;

FIG. 15A is a top view of the container top;

FIG. 15B is a side view of the container top;

FIG. 17 is a perspective view of a sterile bowl of the present invention;

FIG. 18 is a perspective view of the lid of the bowl;

FIG. 20 is an exploded perspective view of a further embodiment of the pen of the present invention;

FIG. 21A is a cutaway view of the pen of FIG. 20;

FIG. 21B is a further cutaway view of the pen of FIG. 20;

FIG. 22 is a side view of the pen empty;

FIG. 23 is a side view of the pen holding heated fluid;

FIG. 24 is a side view of the pen with the side bulbs squeezed lightly and a droplet of water being applied to a bioabsorbable plate;

FIG. 25 is a perspective view of a template and plate;

FIG. 26 is a partial perspective exploded view of the driver of the present invention;

FIG. 27 is a partial cutaway side view of the driver clutch of the present invention in the direct drive position;

FIG. 28 is a view taken along line 28—28 of FIG. 27;

FIG. 29 is a partial cutaway side view of the driver clutch of the present invention in the clutch drive position;

FIG. 30 is a view taken along line 30—30 in FIG. 29;

DETAILED DESCRIPTION OF THE PREFERRED EMBODIMENT

Figures 1, 2, 3, 4, 5:
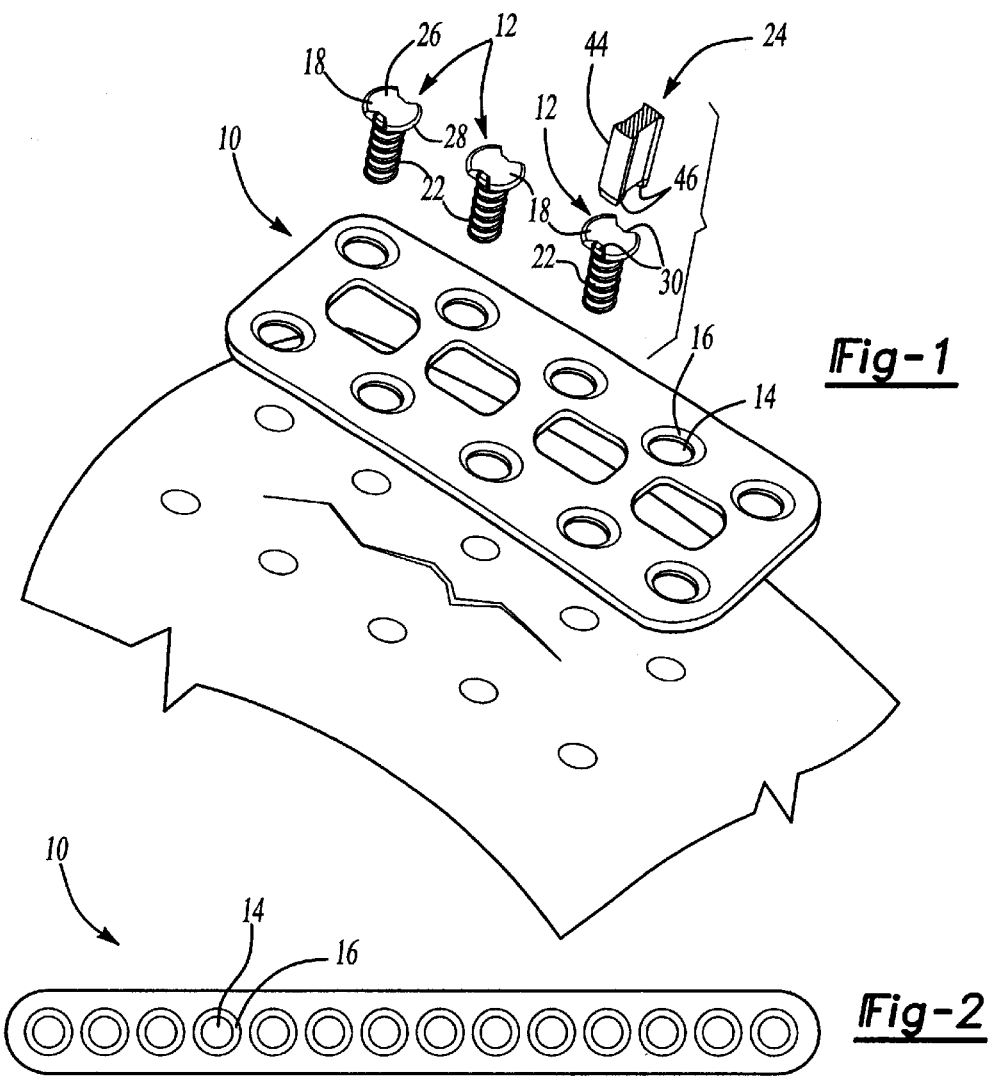
FIG. 1 is a perspective view of the bioabsorbable plate and fasteners of the present invention.
FIGS. 2 through 5 are alternatively shaped bioabsorbable plates of the present invention.

Referring to the Figures, wherein like numerals indicate like or corresponding parts throughout the several views, FIG. 1 shows a bioabsorbable osteosynthesis plate of the present invention at 10. Plates 10 are used to connect bone fragments, which are broken away from each other and hold the bone fragments in place until completely healed. The plates 10 are made from a material, which absorbs into the body after a time so that once the bone fragments have healed in their respective positions a further surgical process is not necessary to go in and remove the plates 10. In the preferred embodiment, the plates are made of 85% Poly L-Lactide, 5% poly D-Lactide and 10% Glycolide. Referring to FIGS. 1 through 5, various examples of the plates 10 are illustrated in different shapes and sizes, which lend themselves to use in specific regions of the head or face or body. It will be appreciated by those of ordinary skill in the art that numerous other shapes could be used. Due to the contours of the human head and face, it is necessary for the plates 10 to be molded or bent to match the specific contour of the bones to which the plates 10 are being applied. Rather than bend the plates 10, thereby creating stress points within the plate 10 and less than perfect contour match-ups, the plates 10 are made from a material which when heated to a certain temperature will allow the plates 10 to be plastically deformed.

The plates 10 have two thermo-chemical solid states. The plate 10 has a first thermo-chemical solid state which is rigid, and a second thermo-chemical solid state which, although still solid, is moldable. The plate 10 will remain at the first thermo-chemical solid state at room temperature and at any temperature below a glass transition temperature. In the preferred embodiment, the plate 10 will remain in the first thermo-chemical solid state until the plate 10 is heated to a temperature in excess of approximately 140 degrees Fahrenheit, or roughly 60 degrees Celsius. When the plate 10 is heated to a temperature exceeding the glass transition temperature, the plate 10 transforms to a second thermo-chemical solid state in which the plate 10 is deformable. In this state, the plate 10 can be molded to a different contour than the plate 10 originally presented. The second thermo-chemical state is still solid, however the plate 10 is sufficiently deformable in the second thermo-chemical state to allow the plate 10 to be molded to a shape more in line with the surface to which the plate 10 will be attached.

After the plate 10 is molded to the shape desired, the plate 10 is allowed to cool below the glass transition temperature, thereby causing the plate 10 to transform back to the first thermo-chemical state. In this state, the plate 10 will now rigidly hold the new shape to which the plate 10 has been molded. Now, the plate 10 will retain the shape that the plate 10 has been deformed to without displaying any weakening in the structure of the plate 10.

The plate 10 is held in place by fasteners 12. The fasteners 10 are generally screw like and are inserted through openings 14 within the plates 10 and threaded into holes drilled into the bone. The plate 10 has a relief area 16 around the openings 14. The plate 10 includes at least two openings 14 for receiving a fastener 12 to hold the plate 10 in place. A head portion 18 of the fastener 12 will fit within the relief area 16. In this way, the head portion 18 of the fastener 12 will not protrude above the surface of the plate 10. This feature is important because any protrusions from the plate 10 may be visible through the skin of a patient when the plates 10 are used to repair bone structure.

An additional feature of the present invention is that the relief area 16 around the openings 14 within the plates 10 has a concave curved contour. See FIGS. 7 and 8. This feature allows the fasteners 12 to seat more solidly within the relief area 16 and produces lower stress than traditional tapered holes. It is desirable that there is at least line contact entirely around the circumference of the opening 14 in the plate 10 between the head portion 18 of the fastener 12 and the plate 10. If the head portion 18 of the fastener 12 is only contacting the plate 10 on one side of the relief area 16 then uneven stresses will occur within the plate 10. Uneven stresses make the plate 10 more likely to fail or the stresses can be transferred through the plate 10 to the underlying bone. Often, the fasteners 12 cannot be inserted perfectly perpendicular to the plate 10. The concave contour of the relief area 16 allows preferably surface contact, but at least line contact, between the plate 10 and the fastener 12 around the entire circumference of the relief area 16 even when the fastener 12 is inserted at an angle not perfectly perpendicular to the plate 10.

It is an additional feature of the present invention, to color code the plates 10 for easy identification during a surgical procedure. Currently there is no easy way to identify the plates 10 in order to minimize confusion. The plates 10 can come in several different sizes and shapes depending on the specific application. By manufacturing the plates 10 with a unique color associated with each unique shape and size, confusion will be minimized and time will be saved. The color-coding will allow a doctor or nurse to identify and request the specific plate 10 and to better locate and implant screws and plates in vivo.

Additionally, the package containing bioabsorbable plates 10 are marked with an identification mark, not shown. The mark allows the package with the plates 10 to be identified more precisely. The identification mark is preferably a simple designation indicating the size and shape of the desired plate 10 in a manner that will allow the nurse or doctor to easily read and recognize the identification mark and the corresponding mark on the package containing the plate 10.

Referring to FIGS. 6A through 10, an additional aspect of the present invention is an improved fastener 12 for attaching the plates 10 to the bone. The improved fastener 12 has a generally screw like shape and is made from bioabsorbable material such as the plates. The fastener 12 includes a threaded shaft portion 22 for engagement with a hole drilled into bone, and a head portion 18 for engagement with the relief area 16 around the opening 14 in the plate 10. Referring to FIGS. 6A, 8 and 9, specifically, the head portion 18 of the improved fastener 12 has a convex curved shape on a bottom surface for engagement with the concave curved portion of the relief area 16 around the opening 14 in the plate 10.

As described above, the curved surface of the relief area 16 and the head portion 18 provide for more effective engagement of the head portion 18 of the fastener 12 with the plate 10. Specifically, these features facilitate full circumferential contact between the bottom surface of the head portion 18 of the fastener 12 and the relief area 16 of the plate 10. Full surface contact around the entire circumference, even when the fastener 12 is inserted an angle, which is not perpendicular to the plate 10, reduces the likelihood of concentrated stresses building within the plate 10 or being transferred to the underlying bone structure.

An additional feature of the improved fastener 12 is greater strength. The improved fastener 12 is designed to be structurally stronger than prior art fasteners, and includes a head portion 18 which is designed for improved engagement with a driver 24. See FIG. 11. Referring to FIG. 6A, specifically, the top surface 26 of the fastener head 18 is designed such that when the driver 24 is used to thread the fastener 12 into a drilled hole, the forces are concentrated at an outer diameter 28 of the head portion 18. The fastener 12 includes notches 30 on opposing sides at the outer diameter 28 of the head portion 18. These notches 30 accommodate the driver 24 for threading the fastener 12 in place. Additionally, the notches 30 are shaped so the contact surfaces of the fastener head 18 fall on a line 32, which does not run through the center of the fastener head 18. Specifically, the notches include side walls 34 and an inner wall 36. The side walls 34 provide a contact surface for the driver 24 and fall on lines 32 that cross at a point outside the center line of the head 18 of the fastener 12. This design results in greater compressive stresses within the head 18, thereby reducing the risk of fracture during application.

In prior art designs the forces are concentrated along lines that go through the center of the fastener 12. This condition creates tensile forces within the fastener head 18 that tend to cause failure and separation from the shaft 22 of the fastener 12. This is a very big concern since when the head portion 18 breaks from the shaft 22, there is not an easy way to remove the broken shaft 22 from the bone structure. By diverting the forces away from the center of the fastener 12 and concentrating the forces along lines 32 that do not run through the center of the fastener head 18, compressive forces are created within the fastener head 18. The compressive stresses are less likely to cause failure within the fastener 12 thereby reducing the risk that the head portion 18 will break off when the fastener 12 is inserted.

Additionally, the design of the fastener head 18 is lower in profile than prior art designs. Prior art fasteners use a driver such as a philips or hex head screwdriver to insert the fasteners 12 and must have more material in the head portion of the fastener 12 in order to accommodate the hole needed for insertion of the screwdriver. The fastener 12 of the present invention does not have an intrusive hole for insertion of the driver 24 and therefore is much thinner in profile. When the low profile fastener 12 is inserted, there is less likelihood that the head portion 18 will protrude above the plate 10 thereby allowing the fastener head 18 to rest completely countersunk so it is not above the top surface of the plate 10.

Additionally, the depth of the notches 30 allows the features of the driver 24 that engage the head portion 18 of the fastener 12 to rest entirely within the diameter of the head portion 18. This reduces the risk of damaging the plate 10 when the fastener 12 is being threaded into place.

The fastener 12 can be any one of a plurality of sizes. In the preferred embodiment, the fastener 12 is one of three specific sizes. Preferably, the fastener 12 is either 1.7 millimeters, 2.2 millimeters and 2.6 millimeters. This dimension is a measurement of the diameter of the threads of the fastener 12. Fasteners 12 of either dimension have similar head portions 18, so either size is equally appropriate for use with any plate 10. Primarily the 1.7 millimeter fastener 12 is used in all applications. The primary purpose for the 2.2 millimeter fastener 12 is as a repair fastener 12. If the hole within the bone structure becomes stripped of the threads, then a 1.7 millimeter fastener 12 will no longer thread securely into the stripped hole. When this happens, a larger hole can be drilled and tapped within the bone, the larger hole being appropriate to accommodate the larger 2.2 millimeter fastener 12. In the preferred embodiment, the different sized fasteners 12 are marked with biodegradable colored paint. Similar to the discussion above concerning color coding of the plates 10, color coding of the fasteners 12 will allow easy and quick identification of different fasteners 12, as well as making the fasteners 12 easier to see and to be able to find the plates 10 and fasteners 12 in the body during surgery.

Referring to FIG. 6B, another aspect of the improved fastener 12 is that the head portion 18 includes features to facilitate mating engagement with the driver 24 for inserting the fasteners 12 into the drilled hole within the bone structure. The rear wall 36 of the notches 30 provides a gripping surface which frictionally engages with the driver 24, which will be described, in greater detail below. In FIG. 9, the gripping surface includes an optional protrusion 40, which can be used to facilitate the frictional interaction between the driver 24 and the fastener 12. The gripping surface of rear wall 36 allows the fastener 12 to be placed within the grasp of the driver 24 and held there until the fastener 12 is installed. This surface of rear walls 36 is separate from the driving surfaces, which are defined by the side walls 34 of the notches 30. Unlike typical fasteners in which the gripping surface and driving surface are the same, in this system the two are separated which reduces stresses in the fastener 12 and permits independent fine-tuning of each surface.

Referring to FIGS. 11–14, it is an additional object of the present invention to provide a driver 24 for inserting the fasteners 12 within the bone structure for fastening the plate 10 thereto. The driver 24 includes a grip 42, and an operative end 44 which includes fingers 46 for engagement with features on the fastener 12 to hold the fastener 12 to the driver 24 as the fastener 12 is brought into contact with the bone structure. The driver 24 has a generally screw-driver like appearance, however the operable end 44 of the driver 24 includes fingers 46 which are designed to fit within the notches 30 along the side of the head portion 18 of the fastener 12. The fingers 46 of the driver 24 are not long enough to protrude beyond the base of the head portion 18, and the thickness of the fingers 46 is less than the depth of the notches 30 so that the fingers 46 will not contact the plate 10 during insertion of the fastener 12.

Referring to FIG. 14, the sides 50 of the fingers 46 are angled to match the angled side walls 34 of the notches 30 on the head portion 18 of the fastener 12. When the driver 24 is rotated, the forces are transferred to the contact surfaces within the head portion 18 to force the fastener 12 to thread into the hole. The fingers 46 can also include a recess 52 for receiving protrusion 40 on the fastener 12 to facilitate better frictional engagement between the fastener 12 and the fingers 46 of the driver 24.

Additionally, the driver 24 has a clutch mechanism 54 that is engaged at the discretion of the user. The clutch mechanism 54 limits the amount of torque that the driver 24 can transfer to the fastener 12 thereby preventing inadvertent over-tightening of the fastener 12, which can cause the fastener 12 to break. The driver 24 of the present invention provides a selective clutch that can be engaged or disengaged at the user's discretion. The driver 24 includes a switch 56 allowing the user to activate or deactivate the clutch mechanism 54.

With reference to FIGS. 26 through 30, the clutch 54 of the preferred embodiment is illustrated. The clutch 54 includes switch 56 connect to a control ring 310. The control ring 310 is mounted so that it can slide back and forth within handle 15. The end 312 of ring 310 is open and receives the end 314 of drive control 316 when ring 310 is slid against the drive control 316. The drive control 316 is split to form two separate fingers 318, 320 which are somewhat flexible. A torque band 322 is provided to adjust the amount of torque applied by the driver 24. Torque is adjusted by sliding the band 322 along the fingers 318, 320. As the band 322 is moved closer to end 314, the torque applied increases. The torque band is preferably made of metal with the torque being preset at manufacture.

A drive blade 324 is mounted between fingers 318, 320. The drive blade 324 is operatively connected to the grip 42 through connector shaft 326 and to the shaft 372 of operable end 44.

In use, movement of switch 56 provides either direct drive or clutch drive operation. In direct drive, the torque applied to handle 15 is directly transferred to the operative end 44 of the driver. In clutch drive, the torque applied to handle 15 will cause slipping between the handle 15 and the operative end 44, if a predetermined torque is exceeded.

Direct drive is illustrated in FIGS. 27 and 28. As illustrated, the control ring 310 has been slid over the end 314 of drive control 316. This causes fingers 318, 320 to be pressed against blade 324 rotatably locking them together. In operation, the handle 15 is held and the user rotates grip 42 with his or her fingers to rotate the operative end 44. Any torque applied to grip 42 will be transmitted through locked fingers 318, 320 and directly to blade 324, which is connected to shaft 326. Shaft 326 is directly connected through a chuck 370 to the shaft 372 of operable end 44, see FIG. 11A.

With reference to FIG. 29, the driver 24 is illustrated in the clutch drive mode. In this mode, the ring 310 is disengaged from end 314. The fingers 318 and 320 are urged against the blade 324 by the band 322 through the resiliency of fingers 318 and 320. In the preferred embodiment, fingers 318 and 320 are made of metal, but due to their relative thickness, they are slightly flexible. When torque is applied to grip 42 in the clutch drive mode, the arms 318, 320 continually press against blade 324 until a predetermined torque is exceeded. When the predetermined torque is exceeded, the fingers 318 and 320 spread open to allow blade 324 to slip between them. In this way, no more than a predetermined amount of torque can be applied to the operative end 44.

With reference to FIG. 15, a pair of improved forceps 58 are illustrated for handling the plates 10. Traditional forceps typically have small sharp features, which can damage the relatively soft plates 10. The forceps 58 of the present invention have generally flat protruding portions 60 for grasping the plates 10 which are large enough and blunt enough to prevent damaging the softened plates 10. Specifically, the forceps 58 are generally like a traditional set of forceps, however, the operable ends of the forceps 58, include large protruding portions 60 to gently grab the plates 10. It is important to avoid damaging the plates 10 when handling them, as dents within the plates 10 will cause stresses within the plates 10 that can affect the integrity of the plates 10.

More specifically, the forceps 58 include a pair of elongated arms 62 in adjacent lengthwise relationship with each other. Each arm 62 includes a first end 63 and second ends 64 and 66. The arms 62 are secured to each other at the first ends 63. The second ends 64 and 66 of arms 62 are disposed at a distance from each other. Each arm 62 includes a flat protruding portion 60 attached at the second end 64 and 66 and the protruding portions 60 are oriented parallel to each other. Each arm 62 further includes a handle portion 68 extending from the first end 63 to provide a gripping surface 71 for holding the forceps 58 and to squeeze the arms 62 toward each other to bring the faces 70 of flat protruding portions 60 into contact within the plate 10. A neck portion 72 extends between the handle portion 68 and the flat protruding portion 60 of each arm 62. In the preferred embodiment, the neck portion 72 extends from the handle portion 68 at an angle. The angle between the neck portion 72 and the handle portion 68 being less than 180 degrees.

Figure 16A:
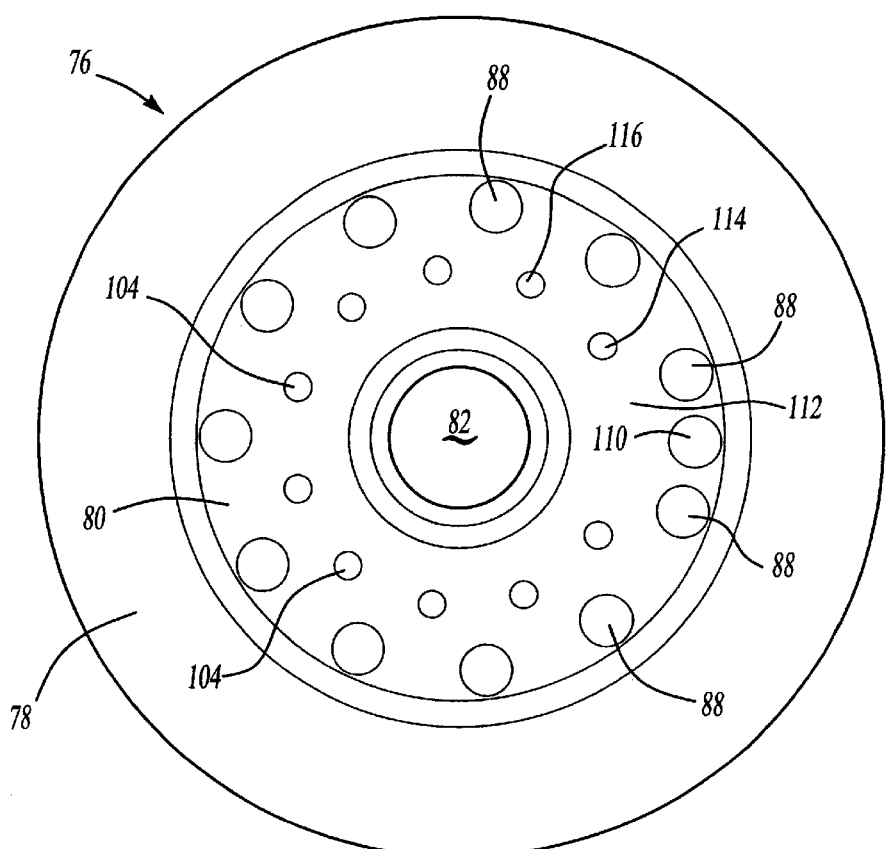
FIG. 16A is a top view of the base.
Figure 16B:
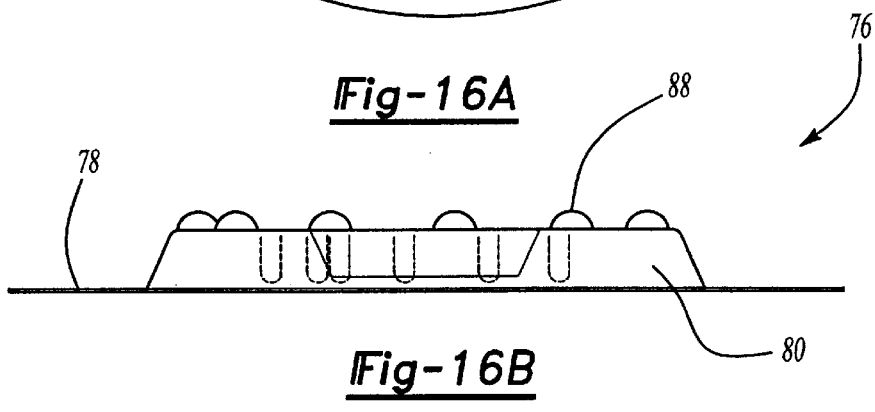
FIG. 16B is a side view of the base.

Referring to FIGS. 15A, 15B, 16A and 16B, a container 76 is illustrating for the fasteners 12. The container 76 presents the fasteners 12 in a manner appropriate for engagement with the driver 24, thereby eliminating any manual handling of the fasteners 12. Referring to FIGS. 16A and 16B, the container 76 includes a base 78 that is generally flat and includes a raised central portion 80. The raised central portion 80 includes a recess 82 located at the center. With reference to FIGS. 15A and 15B, a lid 84 is mounted rotatably to the base 78. The lid 84 is generally bowl shaped and is sized to fit over the raised central portion 80 of the base 78. The lid 84 further includes an annular ridge portion 86 extending downward from the center of the lid 84. The recess 82 within the base 78 is adapted to receive and frictionally secure the annular ridge portion 86 of the lid 84, thereby rotatably securing the lid 84 to the base 78.

The base 78 further includes a plurality of raised detents 88 spaced radially around an outer perimeter of the raised central portion 80. The lid 84 includes a raised annular channel 92 extending around an outer perimeter 94 of the lid 84 such that the raised detents 88 on the base 78 are received within the raised annular channel 92 of the lid 84 when the lid 84 is secured to the base 78. The raised annular channel 92 does not extend about the entire circumference of the lid 84. Rather, the raised annular channel 92 of the lid 84 has a first end 96 and a second end 98 with a space 100 located between them. A semi-spherical recess 102 is located in the space 100 between the first and second ends 96, 98 of the raised annular channel 92. The semi-spherical recess 102 is shaped to receive one of the plurality of detents 88 spaced around the base 78 when the lid 84 is secured thereto.

The base 78 also includes a plurality of apertures 104 spaced radially around the raised central portion 80 of the base 78 and located between the recess 82 at the center of the base 78 and the raised detents 88 spaced radially about the outer perimeter of the base 78. The apertures 104 are funnel shaped cavities adapted to receive a fastener 12 therein. The funnel shape is preferred so the aperture 104 can accommodate the fastener 12 in a vertical orientation with the head portion 18 presented upward. The depth of the apertures 104 is sufficient to allow the fastener 12 to sit within the aperture 104 with the top surface 26 of the head portion 18 of the fastener 12 roughly level with the top surface of the raised central portion 80 of the base 78. When the lid 84 is secured to the base 78, the surface of the lid 84 is in close proximity to the top surface of the raised central portion 80 of the base 78, thereby keeping the fasteners 12 from falling out of the apertures 104.

The lid 84 includes a pair of openings 106, 108 to allow the driver 24 to be inserted to engage and remove the fasteners 12 from the container 76. The openings 106, 108 are spaced radially about the lid 84 between the center portion of the lid 84 and the raised annular channel 92 extending about the circumference of the lid 84. The openings 106, 108 are located to fall immediately above an aperture 104 when the lid 84 is rotated about the base 78. The openings 106, 108 are spaced from each other so that the lid 84 can be rotated to a position where each opening 106, 108 is immediately over an aperture 104 position. The openings 106, 108 are generally circular and are large enough to allow easy insertion of the driver 24 and removal of a fastener 12. The semi-spherical recess 102 located at the outer perimeter 94 of the lid 84 is located radially between the openings 106, 108.

Referring to FIG. 15A, the lid 84 of the container 76 is rotated until at least one of the openings 106, 108 within the lid 84 is directly above a fastener 12 held within the container 76. The driver 24 is inserted within the opening 106, 108 until the fingers 46 engage the fastener 12. Once the fastener 12 is within the grip of the fingers 46, the driver 24 is withdrawn from the opening 106, 108 in the container lid 84. The fasteners 12 are held within the apertures 104 and suspended by the underside of the head portion 18 within the base 78 of the container 76 so that normal transportation of the container 76 will not jar the fasteners 12 out of aperture 104. The head portion 18 of the fastener 12 is trapped between the lid 84 and the aperture 104. However, the fasteners 12 are also held loosely enough to allow the grasping force of the driver 24 to pull the fastener 12 from the aperture 104 and extract the fastener 12 from the container 76.

The base 78 includes a starting position detent 110 which is located between two of the otherwise equidistantly spaced detents 88 about the circumference of the base 78. The base 78 also includes a vacant area 112 along the top surface. The vacant area 112 is essentially a break in the radially spaced aperture positions. The starting position detent 110 is spaced radially in line with the vacant area 112. When the container 76 is shipped, fasteners 12 will reside in each of the apertures 104. The lid 84 will be secured to the base 78 with the starting detent 110 disposed within the semi-spherical recess 102 to hold the lid 84 in that position. When the lid 84 is in this starting position, the openings 106, 108 both fall over the vacant area 112, therefore, no fasteners 12 are exposed and all fasteners 12 are held in the apertures 104 by the lid 84. When the lid 84 is rotated the semi-spherical recess 102 will move from the starting detent 110 to a first of the equidistantly spaced detents 88. When the recess 102 reaches the first detent 88 and snaps into place, the person rotating the lid 84 will feel the lid 84 snap into place which will signal to that person to cease rotation of the lid 84. Without an external force, the semi-spherical recess 102 and the detents 88 will keep the lid 84 from rotating out of place.

Once the lid 84 has been rotated one position a first 106 of the two openings 106, 108 will have rotated to a position immediately over a first aperture 114 with a fastener 12 therein. A second 108 of the two openings 106, 108 is still over the vacant area 112. If the lid 84 is rotated one more position, the first opening 106 will move to a position between the first aperture 114 and a second aperture 116 while the second opening 108 will still remain over the vacant area 112. In this position, the openings 106, 108 are on either side of the first aperture position 114, and no apertures 104 or fasteners 12 are exposed. If the lid 84 is rotated one more position, then the first opening 106 will move over the second aperture 116, thereby exposing the fastener 12 therein and the second opening 108 will move over the first aperture 114 location. It should be understood that rotating the lid 84 one position can either be where the semi-spherical recess 102 is positioned between consecutive detents 88 on the base 78 or where the semi-spherical recess 102 is over a detent 88. In this way, the lid 84 can be rotated around the base 78 to expose either one or two fasteners 12 at a time, and allowing the lid 84 to be rotated to a position where the openings 106, 108 are located between apertures 104 so that no fasteners 12 are exposed.

The container 76 is preferably made from a plastic material, and is colored to contrast the color of the fasteners 12 that are held within. The contrasting color helps a doctor or nurse to visibly see the fasteners 12 within the container 76 and will make it easier to retrieve the fasteners 12 using a driver 24.

A sterile bowl system 118 is illustrated in FIG. 17 for holding heated fluid 120. The bowl 118 is portable and can be located nearby, within the immediate sterile area of the surgical procedure. The material that the plates 10 are made from transforms from a rigid solid state to a plastically deformable solid state when heated above a specific temperature. This feature allows the plates 10 to be molded to fit specific contours of the bone structure. It is important that the plates 10 match the contour of the bones, which are being repaired as closely as possible to insure that the bones heal correctly and to prevent features of the plates 10 from being visible through the skin of the patient when the procedure is complete. In practice, the plates 10 are taken to the point of use, and then heated to the deformable temperature so they can be molded to the exact contour required. The fluid 120 is preferably water, which improves the heat transfer to the plates 10.

The portable sterile bowl 118 includes a base 122 and a reservoir 124 for holding the heated fluid 120. The bowl 118 also includes a heating element, not shown, for heating and maintaining the fluid 120 at the appropriate temperature. In practice, the bowl 118 can be placed within the sterile confines of the surgical area to allow plates 10 to be dipped and molded during the procedure. Due to the characteristics of the plate 10 material, the plate 10 will transform to a plastically deformable state almost immediately upon being dipped within the heated fluid 120, and will cool down to the rigid non-deformable state very quickly after being removed from the heated fluid 120. The portable bowl 118 is small enough to be placed within the general area of the surgical procedure to allow the doctor to easily dip the plates 10 and make adjustments to the shape of the plates 10 throughout the procedure. The bowl 118 is large enough to allow the entire plate 10 to be dipped within the bowl 118 so the entire plate 10 can be shaped to the contour necessary.

In order to keep the sterile bowl 118 compact, the bowl 118 includes only the base 122, the reservoir 124, and a heating element for keeping the fluid 120 within the bowl 118 heated. A controller 128 for the bowl 118 is located away from the bowl 118 and outside of the immediate surgical area. The controller 128 for the bowl 118 communicates with the bowl 118 to monitor and maintain the temperature of the fluid 120 and allow the temperature setting to be adjusted manually or to be discretely set during manufacture. The bowl 118 is small enough to be placed within the immediate surgical area, therefore making it easier to maintain a sterile environment as the plates 10 are repeatedly dipped and shaped. The bowl 118 keeps the fluid at a constant temperature to insure efficient and convenient heating of the plates 10 throughout the procedure. Additionally, the bowl is easy to sterilize since the control component 128 does not have to be sterilized.

In the preferred embodiment, the bowl 118 is covered by a two-piece lid 130. See FIG. 18. The lid includes a first section 132 and a second section 134. The lid sections 132, 134 mate together at edges 136. The first lid section 132 has two recesses 138, which allow the user to place tools into these recesses 138 when they are not in use. The two sections 132, 134 also allow the bowl 118 to be fully closed, partially open or fully open.

Figure 19:
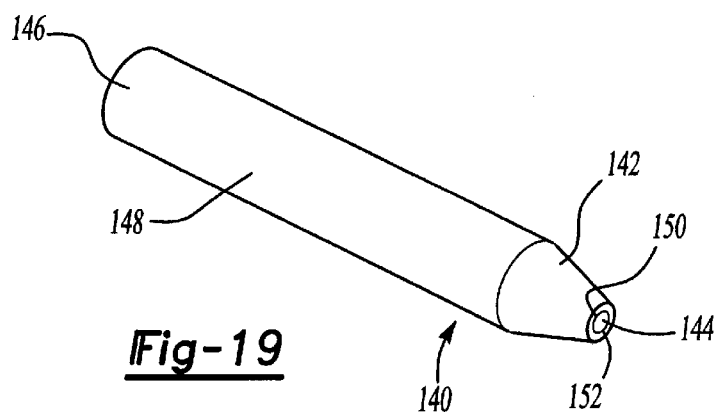
FIG. 19 is a perspective view of a pen device of the present invention.
Figure 31:
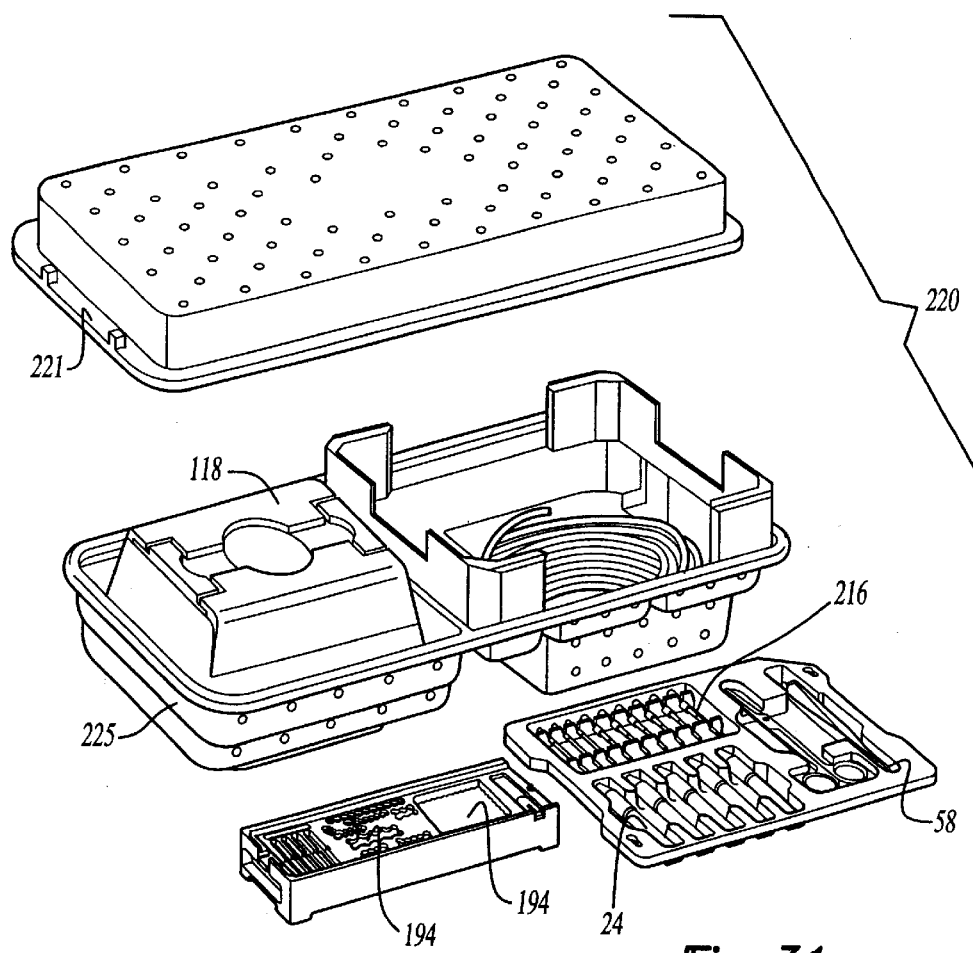
FIG. 31 is a perspective view of the kit of the present invention.
Figure 32:
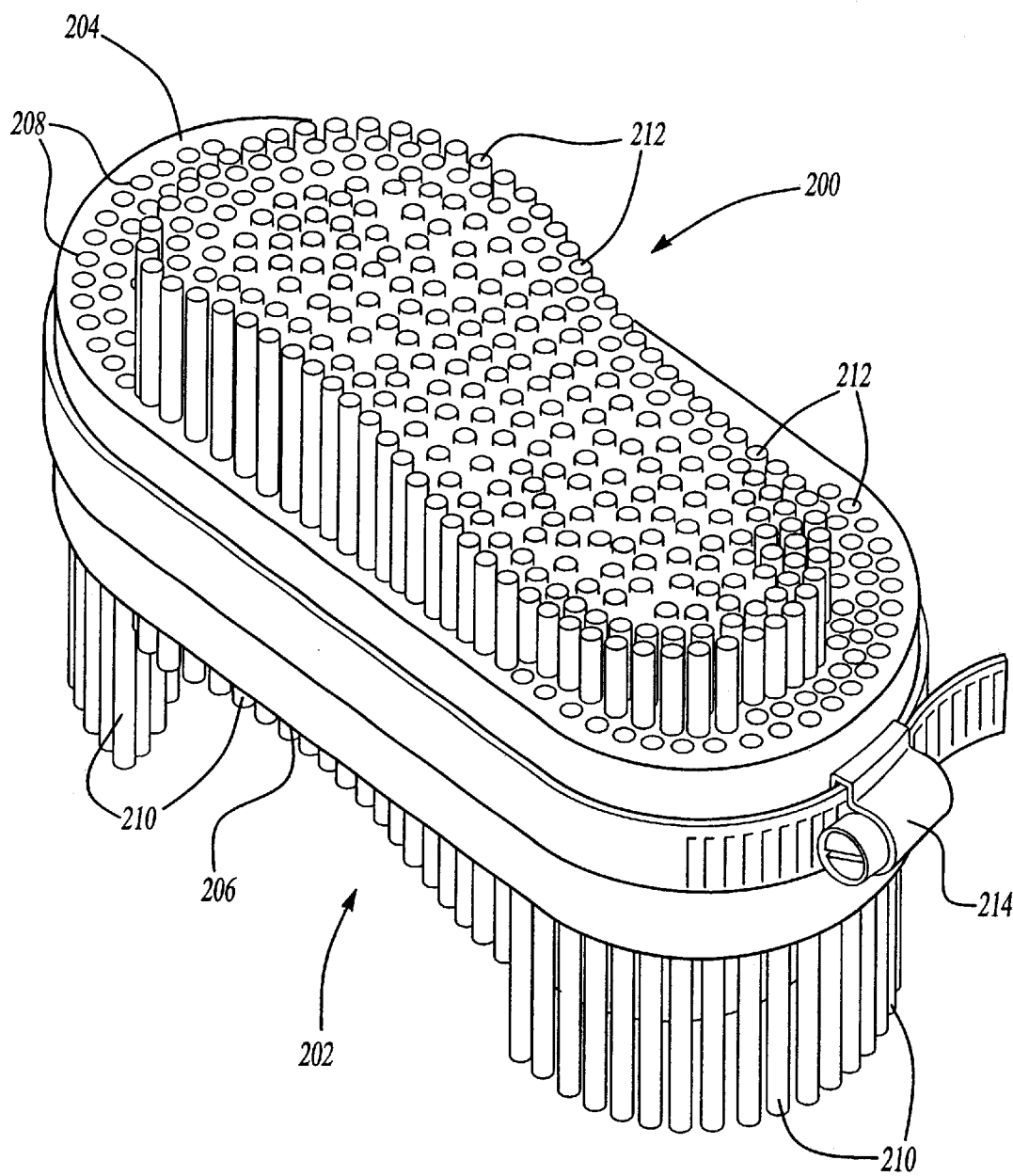
FIG. 32 is a partial cutaway perspective view of an alternative template.

With reference to FIG. 19, the present invention also includes an apparatus or tool 140 for applying the heated fluid 120 to a localized portion of the plates 10 to heat the localized portion of the plate 10 to a temperature that will allow the plate 10 to be plastically deformed. The tool 140 includes a front end 142 with a tip, or tip portion 144, a rear end 146, a shaft portion 148 interconnecting the front 142 and rear 146 ends, and a cavity 150 extending from the tip portion 144. The cavity 150 allows surface tension to create a vacuum to hold a droplet of heated fluid 120 to the tip 144 when the tool 140 is dipped within a volume of heated fluid 120. It should be understood that the tool 140 acts as a heat sink to hold heat for transfer to the plate 10. The fluid 120 at tip portion 144 acts as a bridge to transfer the heat from tool 140 to the plate 10.

The tip 144 can also include a roughened surface 152 surrounding the cavity 150 to assist in holding the droplet of water to the tip 144. In contrast to the bowl 118 as described above, the tool 140 is used to apply heated fluid 120 between the tip 144 of the tool 140 and a plate 10, i.e., the fluid creates a thermal bridge, to improve heat transfer from the tip 144 to a localized portion of the plate 10. The tip 144 is preferably made from a thermally conductive autoclavable metal that will heat up when dipped within the heated fluid 120. When the droplet of water is touched to the plate 10, the heat from the tip 144 is transferred to the plate 10 through the fluid 120. This is necessary when the plate 10 has already been partially secured in place, and further shaping of the plate 10 is necessary to conform the plate 10 to the finer details of the bone structure to which the plate 10 is fastened.

With reference to FIG. 20, an alternative and preferred tool 156 could include a passage 154 to allow heated fluid 120 to be drawn upward into the tool 156 until the operator wishes to present the fluid 120 to a plate 10. The alternative tool 156 also includes a front end 158 with a tip 160, a rear end 162, and a shaft portion 164 extending therebetween. The tool 156 includes a bulb 178 for drawing the heated fluid 120 into the tip 160 to allow the fluid 120 to be presented from the tip 160 in a controlled manner. The front end 158 includes a fluid channel 170 with a first end 172 at the tip 160 and a second end 174 at a position along the shaft portion 164. The fluid channel 170 extends between the first end 172 and the second end 174 to create a passage therebetween. The fluid channel 170 is operable to receive and hold the heated fluid 120 that is drawn up into the tool 156. The tool 156 can also include a feature 192 to allow the tool 156 to hang onto or within the bowl 118 until needed.

The tool 156 includes a sleeve 176 that extends radially around the housing 166 with at least one compressible bulb 178 extending therefrom. The bulb 178 defines a cavity 180 between the bulb 178 and the housing 166. The housing 166 includes an opening 182 intersecting the cavity 180 and the fluid channel 170. The tool 156 further includes a pair of O-rings 184 for creating a seal between the housing 166 and the core element 168. The O-rings 184 are located along the core element 168 such that the cavity 180, the opening 182, and the second end 174 of the fluid channel 170 are all located between the O-rings 184. The cavity 180, the opening 182, and the fluid channel 170 define a variable volume chamber.

In operation, the bulb 178 is squeezed to reduce the volume of the variable volume chamber 180. The tip 160 of the tool 156 is dipped within a body of heated fluid 120 and the bulb 178 is released. When the bulb 178 is released the variable volume chamber 186 expands and draws fluid 120 upward into the fluid channel 170. The tool 156 can then be removed from the fluid 120 and when a droplet of fluid 120 is desired, the operator can gently squeeze the bulb 178 to dispense the fluid 120 in a controlled manner.

The tool 156 illustrated in FIGS. 22 through 25 can also include a branch channel 188 extending perpendicular to the fluid channel 170. The branch channel 188 provides a path for air to enter the fluid channel 170 to break the suction between the fluid channel 170 and a drop of fluid 120 that has been dispensed at the tip 160. When the bulb 178 is released, the variable volume chamber 180 expands, and would normally draw the fluid 120 back up into the fluid channel 170. The branch channel 188 allows air to enter so the droplet of fluid 120 that is presented at the tip 160 will remain there held by surface tension when the bulb 178 is released. The core 164 of the tool 156 is preferably made from non-corrosive metal and the housing 166 is made from an autoclavable plastic. The tool 156 is designed such that the components can be taken apart and sterilized periodically.

Another optional feature of the alternative tool 156 is a heating element (not pictured). The heating element is mounted within the housing 166 of the tool 156 to provide heat directly to the core 164. In this way, the tool 156 can draw in a volume of fluid 120 and the fluid 120 is kept at an appropriate temperature while the fluid 120 remains in the tool 156 to insure that the fluid 120 is still at the appropriate temperature when dispensed.

The tool 156 presents a droplet of the heated fluid 120 to an opening at the tip 160 of the tool 156. See FIG. 24. The tool 156 can then be brought within the proximity of the plate 10 and the droplet touched to the specific point upon the plate 10 where further shaping is required. Once again, due to the efficient heat transfer characteristics of the fluid, the heat from the metallic core 164 of the tool 156 will transfer through the droplet of fluid 120 and almost immediately transform the localized area of the plate 10 to a plastically deformable state. The plate 10 can then be shaped to conform to the details of the bone contour and then very quickly cooled down to a rigid state again. The introduction of a droplet of fluid 120 insures full contact across the surface of the plate 10, and results in more efficient heat transfer. The use of a solid heating element brought into contact with the plate 10 would not be as efficient, as different contours within the plate 10 would allow only point contact between the solid element and the plate 10. The alternative tool 156 contains a passive thermal mass, unlike traditional heating systems.

The present invention also provides a template 194 for pre-shaping the plates 10 prior to being applied to the bone structure. Referring to FIG. 25, the template 194 is formed from a very ductile and non-corrosive metal and is generally made to coincide with the outer shape and size of corresponding plates 10. In practice, the template 194 is placed onto the bone structure that is to be repaired, and molded to the contour of the bone structure. The template 194 is easily moldable, so it requires very little effort to form the template 194 to the contours of the bone structure. However, the template 194 is rigid enough to hold the contour shape after the template 194 is removed. When the template 194 is used, an appropriate plate 10 can be selected. The template 194 is shaped as required. The plate 10 and template 194 are then held at one end by tool 58 and dipped into the waterbath 124. See FIG. 25. The heated plate 10 can then be easily adjusted to take the shape of template 194. This allows the plate 10 to be shaped very closely to the bone structure that is to be repaired ahead of time thereby making less alterations necessary once the plate 10 is attached to the bone.

Additionally, the template 194 includes indents 196 along either side of the template 194. The indents 196 will indicate where the fasteners 12 will fall when a plate 10 is formed to the shape of the template 194. This feature allows the template 194 to be placed on the bone structure and moved to a position such that the fastener 12 positions will fall in appropriate locations. This assures that when the plate 10 is shaped to match the contour of the template 194, and subsequently placed to the bone structure, that the fastener 12 locations within the plate 10 will be positioned appropriately.

A still further feature of the invention is a unique coding system which streamlines use of the templates 194 and plates 10 and reduces, if not eliminates, confusion. As discussed, the templates 194 are reusable and facilitate the proper contour of the bioabsorbable plates 10. Each template 194 will include a simplified marking 198, for example, 1.7-A, which will correspond to a specific plate 10. The plates 10 are typically kept outside of the sterile field and the surgeon will call out the simplified marking 198 to an assistant after the surgeon has decided upon the correct plate 10 by using the template 194. The assistant merely has to look for a box or container that has the corresponding simplified marking 198 and withdraw a sterilized plate 10 from the box and through sterile technique provide the surgeon with the correct plate 10, matching the template 194.

An alternative template 200 includes a block 202 having a top 204 and bottom 206 surface and including a plurality of holes 208 extending between the top and bottom surfaces 204, 206. A plurality of pins 210 are inserted within the holes 208, one per hole. The pins 210 are longer than the thickness of the block 202, and include ends 212 that are larger than the holes 208 so the pins 210 can slide back and forth within the holes 208 while being held there.

In use, the block 202 is tilted so all the pins 210 slide to one side of the block 202. The template 200 is then brought into proximity with a bone surface that is to be repaired. The ends 212 of the pins 210 contact the bone surface and as the block 202 is brought further forward the pins 210 slide further into the block 202. The block 202 also includes a locking device 214 that when activated locks the pins 210 in place to prevent any further sliding. When the template 200 has been brought close enough to the bone surface to bring all the pins 210 into contact with the bone surface, the locking device 214 is activated, thereby locking the pins 210 in place. When the block 202 is removed from the bone structure, a three-dimensional profile of the bone surface is captured on the end surfaces of the pins 210. The locking device 214 keeps the pins 210 from sliding, so the surgeon has a three-dimensional model to use when pre-shaping plates 10 to be placed onto the bone.

In the preferred embodiment, the block 202 is made from a semi-elastic material, and the locking device 214 is a band or clamp that wraps around the block 202 to squeeze the block 202 when activated. When the locking device 214 is activated, the block 202 is squeezed, and the holes 208 are squeezed, thereby restricting movement of the pins 210 within the holes 208.

With reference to FIG. 11B, the present invention also includes a single step drill and tap bit 216 for simultaneously drilling and tapping holes within the bone structure for fasteners 12 to be threaded into when securing plates 10. The bit 216 will function as both a drill for making the hole and a tap for adding the threads to the hole. Furthermore, the bit 216 includes helical flutes 219 for more efficient evacuation of bone chips from the hole as the hole is drilled and tapped. Prior art drills and taps use axial flutes, which do not work as efficiently. A build up of chips within the hole during the drill/tap process will affect the quality of the threads in the tapped hole. If the tap is not adequate to allow the fastener 12 to thread into the hole, then the hole cannot be used, and another hole must be drilled. Helical flutes and cutting edges 219 will more effectively drill and tap and facilitate the removal of bone material from the hole thereby creating a cleaner hole and resulting in a better thread. It is to be understood that the diameter of the drill/tap 216 could be any size appropriate to accommodate the fasteners 12 for which the hole is being drilled. The bit 216 has drilling thread forms 217 for defining the threads.

The present invention further has a sterilization tray 220 including all components necessary to repair fractured bone by applying bioabsorbable osteosynthesis plates 10. The tray has a top 221 and base 225. The tray 220 includes for example a portable sterile bowl 118 as well as a tool 140 for applying heated fluid to the bioabsorbable plates 10, this is not illustrated, forceps 58 for handling the plates 10, bits 216 for drilling and tapping holes within the bone structure, a number of templates 194 of each size and style for pre-shaping the plates 10, and drivers 24 for inserting and threading the fasteners 12 within the bone structure to secure the plates 10 thereto.

The present invention provides a method of repairing broken bone. The method includes the steps of providing a bioabsorbable osteosynthesis plate 10 having a first thermo-chemical solid state which is rigid, and a second thermo-chemical solid state which is moldable. The plate 10 is then inserted within a source of heated fluid 120 to heat the plate 10 to the moldable thermo-chemical solid state. After the plate 10 is heated to the moldable thermo-chemical state, the plate 10 is formed to the desired contour and allowed to cool to the rigid thermo-chemical solid state. The plate 10 is then placed to the bone structure to be repaired and fastened thereto.

The method could be modified by including the steps of providing a fastener 12 for attaching the plates 10 to the bone structure, a container 76 for delivering the fasteners 12 to a point of use including a base portion 78 with apertures 104 for holding a plurality of fasteners 12, and a lid portion 84 with at least one opening 106, 108 therein, and a driver 24 for threading the fasteners 12 into the bone structure. Prior to fastening the plate 10 to the bone structure, the lid 84 of the container 76 is rotated until the opening 106 is positioned directly over an aperture 104 with a fastener 12 held therein. The driver 24 is then inserted through the opening 106 in the lid 84 and into the container 76 to engage the fastener 12 held within the aperture 104. The driver 24 is then withdrawn from the container 76 with the fastener 12 held thereto. The driver 24 is then used to apply the fastener 12 to the bone structure by rotating the driver 24 and thereby threading the fastener 12 into the bone structure. Once the fastener 12 is threaded fully into the bone structure the driver 24 is removed from the fastener 12.

The method could be further modified by including the steps of providing a drill bit tool 216 for drilling and tapping a hole for receiving a fastener 12 into the bone structure to be repaired. Prior to threading the fastener 12 to the bone, the drill bit tool 216 is placed to the bone structure and rotated to form a tapped hole in the bone structure prior to applying the plate 10. Once the holes have been drilled and tapped within the bone structure, the plates 10 are applied to the bone structure and fasteners 12 are threaded into the holes using the driver 24.

The method could be further modified by including the steps of providing a template 194 for pre-shaping the bioabsorbable plate 10. Prior to molding the contour of the plate 10, the template 194 is placed to the bone structure and the contour of the underlying bone is molded to the template 194. The template 194 is removed from the bone structure and the heated plate 10 is placed to the template 194 and molded to the contour of the template 194 by submerging them in a water bath or other heat source.

The method could be further modified, wherein the template 194 includes an identification mark 198 designating the size and shape of the template 194, and the bioabsorbable plate 10 or package includes an identification mark designating the size and shape of the plate 10, and the markings 198, on corresponding templates 194 and plates 10 match. The method further includes the steps of reading the identification mark 198 from the template 194 after the template 194 has been contoured to the bone structure and selecting a plate 10 which has an identification mark that matches the identification mark 198 read from the template 194.

The method could be further modified by including the steps of providing a device 156 for localized heating of the plates 10, inserting the device 156 into a volume of heated fluid 120 to heat the device to a desired temperature, drawing an amount of the heated fluid 120 into the device 156 or holding fluid at the tip of the device 156, bringing the device 156 into close proximity to the plate 10, causing a droplet of the heated fluid 120 to form a thermal conductive bridge between the device 156 and the plate, and molding the plate 10 when locally heated to more closely match the contour of the bone structure to be repaired.

The method could be further modified by including the steps of handling the plates 10 with a handling device 58, wherein the handling device 58 includes a pair of flexible elongated arms 62 in adjacent lengthwise relationship with one another, each arm 62 having a first end 64 and a second end 66, the first ends 64 of the arms 62 being secured to one another, the second ends 66 of the arms 62 are disposed at a distance from one another and include a generally flat protruding portion 60, the protruding portions 60 of each arm 62 being oriented parallel to one another, and grasping the plates 10 with the protruding portions 60.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that the invention may be practiced otherwise than as specifically described.

A preferred embodiment of the present invention has been disclosed, however, an individual of ordinary skill in the art would recognize certain modifications would come within the scope of this invention and thus the following claims should be studied in order to determine the true scope and content of the present invention.

What is claimed is:

1. A hand held device for locally heating a portion of a bioabsorbable plate, said device comprising:

a body portion having a hand held section and a tip;

said body portion defining a thermal mass for retaining heat within said body portion for transfer to the bioabsorbable plate;

said tip holding a fluid for bridging said body portion and the bioabsorbable plate to facilitate heat transfer from said body portion to the bioabsorbable plate, wherein said tip has a roughened surface for retaining the fluid to said tip.

2. The hand held device as set forth in claim 1, further including a cavity for retaining the fluid to said tip.

3. The hand held device as set forth in claim 2, wherein said roughened surface of said tip surrounds said cavity on said tip to provide additional surface area for holding the fluid.

4. The hand held device as set forth in claim 1, wherein said body portion includes a fluid channel, said fluid channel including a first end at said tip and extending to a second end at a position within said body portion thereby creating a passage therebetween, said fluid channel being operable to receive and hold the fluid to be dispensed from said tip.

5. The hand held device as set forth in claim 4, further including a sleeve extending about said body portion and including at least one hollow compressible bulb extending therefrom to define a cavity between said compressible bulb and said body portion, and said body portion including at least one opening positioned between said cavity and said second end of said fluid channel for allowing fluid communication between said cavity and said fluid channel.

6. The hand held device as set forth in claim 5, wherein said body portion includes a pair of o-rings for creating a seal between said body portion and said sleeve, said o-rings being spaced along said body portion such that said cavity, said opening, and said second end of said fluid channel are disposed therebetween, whereby said cavity, said opening, and said fluid channel define a continuous variable volume chamber with only one aperture, said aperture being said first end of said fluid channel.

7. The hand held device as set forth in claim 6, wherein said fluid channel includes a branch channel extending from said fluid channel to a point adjacent said tip for allowing suction between said fluid channel and the fluid at said tip to be interrupted.

8. The hand held device as set forth in claim 5, wherein said body portion that defines said thermal mass is made from a non-corrosive metal and said sleeve is made from an autoclavable insulating material.

9. The hand held device as set forth in claim 4, wherein said body portion includes a heating device for keeping said body portion and the fluid that is within said fluid channel at a pre-determined temperature until the heated fluid is dispensed.

10. The hand held device as set forth in claim 1, wherein said body portion includes a heating device for keeping said tip and the fluid that is within said tip at a pre-determined temperature until the heated fluid is dispensed.

11. A hand held device for locally heating a portion of a bioabsorbable plate, said device comprising:

a body portion having a hand held section and a tip;

said body portion defining a thermal mass for retaining heat within said body portion for transfer to the bioabsorbable plate;

said body portion including a fluid channel, said fluid channel including a first end at said tip and extending to a second end at a position within said body portion thereby creating a passage therebetween, said fluid channel being operable to receive and hold a fluid to be dispensed from said tip;

a sleeve extending about said body portion and including at least one hollow compressible bulb extending therefrom to define a cavity between said compressible bulb and said body portion, and said body portion including at least one opening positioned between said cavity and said second end of said fluid channel for allowing fluid communication between said cavity and said fluid channel; and said tip holding the fluid for bridging said body portion and the bioabsorbable plate to facilitate heat transfer from said body portion to the bioabsorbable plate.

12. The hand held device as set forth in claim 11, wherein said body portion includes a pair of o-rings for creating a seal between said body portion and said sleeve, said o-rings being spaced along said body portion such that said cavity, said opening, and said second end of said fluid channel are disposed therebetween, whereby said cavity, said opening, and said fluid channel define a continuous variable volume chamber with only one aperture, said aperture being said first end of said fluid channel.

13. The hand held device as set forth in claim 12, wherein said fluid channel includes a branch channel extending from said fluid channel to a point adjacent said tip for allowing suction between said fluid channel and the fluid at said tip/y be interrupted.

14. The hand held device as set forth in claim 11 wherein said tip has a roughened surface for retaining the fluid to said tip.

15. A hand held device for locally heating a portion of a bioabsorbable plate, said device comprising:

a body portion having a hand held section and a tip;

said body portion defining a passive thermal mass for retaining heat within said body portion and for transferring of the heat to the bioabsorbable plate;

said tip holding a fluid for bridging said body portion and the bioabsorbable plate to facilitate heat transfer from said body portion to the bioabsorbable plate, wherein said passive thermal mass transfers heat to the fluid and to the bioabsorbable plate without an external electrical connection actively energizing said passive thermal mass to heat up.

16. The hand held device as set forth in claim 15 said body portion that defines said passive thermal mass is made from a non-corrosive metal.

17. The hand held device as set forth in claim 15, further including a cavity for retaining the fluid to said tip.

18. The hand held device of claim 15, wherein said tip has a roughened surface for retaining the fluid to said tip.

19. The hand held device as set forth in claim 15, wherein said tip has a roughened surface surrounding said cavity on said tip to provide additional surface area for holding the fluid.

20. The hand held device as set forth in claim 15, wherein said body portion includes a fluid channel, said fluid channel including a first end at said tip and extending to a second end at a position within said body portion thereby creating a passage therebetween, said fluid channel being operable to receive and hold the fluid to be dispensed from said tip.

21. The hand held device as set forth in claim 20, further including a sleeve extending about said body portion and including at least one hollow compressible bulb extending therefrom to define a cavity between said compressible bulb and said body portion, and said body portion including at least one opening positioned between said cavity and said second end of said fluid channel for allowing fluid communication between said cavity and said fluid channel.

22. The hand held device set forth in claim 21, wherein said body portion includes a pair of o-rings for creating a seal between said body portion and said sleeve, said o-rings being spaced along said body portion such that said cavity, said opening, and said second end of said fluid channel are disposed therebetween, whereby said cavity, said opening, and said fluid channel define a continuous variable volume chamber with only one aperture, said aperture being said first end of said fluid channel.

23. The hand held device as set forth in claim 22, wherein said fluid channel includes a branch channel extending from said fluid channel to a point adjacent said tip for allowing suction between said fluid channel and the fluid at said tip to be interrupted.

24. The hand held device as set forth in claim 21, wherein said body portion that defines said passive thermal mass is made from a non-corrosive metal and said sleeve is made from an autoclavable insulating material.

* * * * *